United States Patent
Sanchez, Jr. et al.

(10) Patent No.: US 8,235,053 B2
(45) Date of Patent: Aug. 7, 2012

(54) IMPLANTABLE PUNCTAL PLUG

(75) Inventors: Robert Joseph Sanchez, Jr., Oceanside, CA (US); Casey Jean Lind, Orange, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 12/877,437

(22) Filed: Sep. 8, 2010

(65) Prior Publication Data
US 2012/0055490 A1 Mar. 8, 2012

(51) Int. Cl.
*A61B 17/00* (2006.01)
*A61M 5/00* (2006.01)

(52) U.S. Cl. ............................ 128/887; 604/8

(58) Field of Classification Search .................. 128/887, 128/846; 604/7–10, 500, 521, 19, 27, 28, 604/264, 294, 107, 108, 289, 290, 540, 541, 604/523, 317, 285, 907; 606/185, 167, 191, 606/107, 108; 623/4.1, 11.11, 23.71, 23.64
See application file for complete search history.

(56) References Cited

U.S. PATENT DOCUMENTS

| | | | |
|---|---|---|---|
| 5,469,867 A | 11/1995 | Schmitt | |
| 5,520,632 A * | 5/1996 | Leveen et al. | 604/9 |
| 5,826,584 A | 10/1998 | Schmitt | |
| 2007/0083146 A1 * | 4/2007 | Murray | 604/8 |
| 2010/0016439 A1 | 1/2010 | Thomas et al. | |
| 2010/0174272 A1 | 7/2010 | Weiner | |
| 2010/0226962 A1 | 9/2010 | Rodstrom et al. | |

OTHER PUBLICATIONS

Labelle, Mark, "Drug Introduction and Placement System," U.S. Appl. No. 12/898,031, filed Oct. 5, 2010, 22 pages.
American Academy of Ophthalmology, "A look at Today's Ideas and Trends," EyeNet Magazine, Oct. 2008, http://www.aao.org/publications/eyenet/200810/news.cfm (10 pages).
Medennium, Medinnium SmartPLUG™ internet catalog, Copyright © 2002 Medennium, http://www.medennium.com/index.php?option=com_content&task=view&id=170; Updated Mar. 10, 2009; (2 pages).
Aetna, Inc., "Punctal Occlusion for Dry Eyes," internet Clinical Policy Bulletin, http://web.archive.org/web/20090403080845/http://www.aetna.com/cpb/medical/data/400_499/0457.html, Web Archive dated Apr. 3, 2009 (7 pages).

* cited by examiner

*Primary Examiner* — Patricia Bianco
*Assistant Examiner* — Tarla Patel
(74) *Attorney, Agent, or Firm* — Russell Henrichs

(57) ABSTRACT

A punctal plug is disclosed, wherein the punctal plug includes a body portion and a retaining portion. The body portion is defined by an open distal end, an open proximal end and a wall portion. The wall portion further includes at least one window extending therethrough. The retaining flange is configured to have an outer periphery that is larger than the outer periphery of the body portion. A method of delivering a therapeutic agent to a patient using a punctal plug is also disclosed.

11 Claims, 3 Drawing Sheets

IMPLANTABLE PUNCTAL PLUG

TECHNICAL FIELD

The present disclosure generally relates to the field of implantable ocular devices, pharmaceutics, and methods of drug delivery to the eye. More particularly, the present disclosure relates to implantable ocular devices for sustained delivery of a therapeutic compound to the eye.

BACKGROUND

Glaucoma is the leading cause of blindness worldwide and the most common cause of optic neuropathy. Various forms of glaucoma leads to elevated intraocular pressure, and may also lead to damage to the optic nerve. If glaucoma or ocular hypertension is detected early and treated promptly with medications that effectively reduce elevated intraocular pressure, loss of visual function or its progressive deterioration can generally be ameliorated. Drug therapies that have been proven useful for the reduction of intraocular pressure include both agents that decrease aqueous humor production and agents that increase the outflow facility. Such therapies may be administrated in a number of different ways.

One example of administrating suitable therapies includes topical application to the eye, such as eye drops. However, one of the limitations of topical therapy is inadequate and irregular delivery of the therapeutic agent to the eye. For example, when an eye drop is applied to the eye, a substantial portion of the drop may be lost due to overflow of the lid margin onto the cheek. Moreover, compliance with a necessary drug regime is also always an issue with this method. For example, for some medications, 4 to 5 applications a day are required to achieve therapeutic drug levels.

Other suitable delivery mechanisms for therapeutic devices include injection at the pars plana. However, aside from discomfort for the patient, this method also requires that the patient return monthly.

Various ocular drug delivery implants have also been employed in an effort to improve and prolong drug delivery. One such example includes a reservoir drug-delivery device. A reservoir drug-delivery device is a device that contains a receptacle or chamber for storing the drug while implanted in the eye. However, reservoir drug devices are difficult to manufacture, difficult to achieve drug content uniformity (i.e., device to device reproducibility, particularly with small ocular devices), and carry the risk of a "dose dump" if they are punctured.

Another type of drug delivery device is a punctal plug device that is inserted into one or more of the tear ducts within the eye. However, because the geometry of the tear duct varies from person to person, there have been problems with plugs migrating within the tear duct. Other issues occur whereby the punctal plugs may inadvertently fall out of the eye.

Accordingly, there exists a need for a therapeutic delivery mechanism that allows for controlled and sustained release of ophthalmic drugs over a predetermined period of time, while sufficiently securing the delivery device within the eye so as to prevent inadvertent migration or removal of the delivery device.

BRIEF SUMMARY

A punctal plug is disclosed, wherein the punctal plug includes a body portion and a retaining portion. The body portion is defined by an open distal end, an open proximal end and a wall portion. The wall portion further includes at least one window extending therethrough. The retaining flange is configured to have an outer periphery that is larger than the outer periphery of the body portion. A method of delivering a therapeutic agent to a patient using a punctal plug is also disclosed.

BRIEF DESCRIPTION OF THE DRAWINGS

Exemplary embodiments of the present disclosure will now by described by way of example in greater detail with reference to the attached figures, in which.

DETAILED DESCRIPTION

Figure 1:
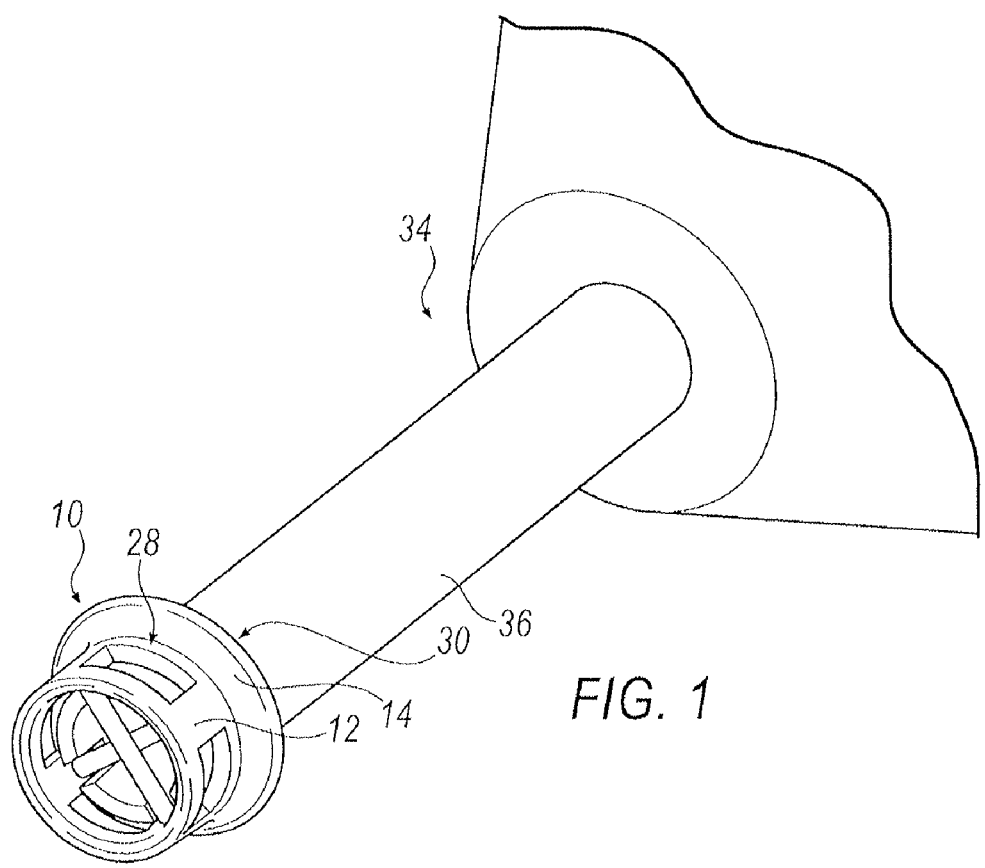
FIG. 1 is a perspective view of a distal end of a delivery device with a punctal plug releasably connected thereto.
Figure 2:
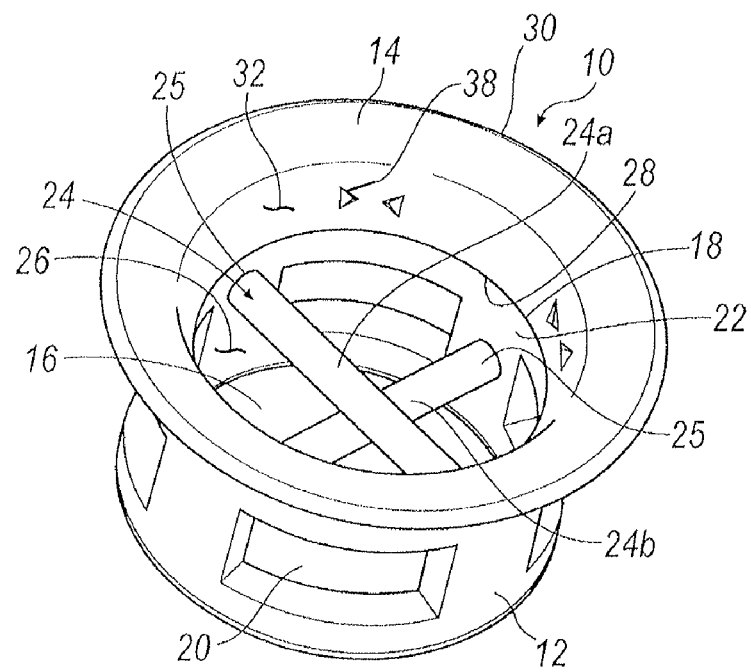
FIG. 2 is a perspective view of an exemplary embodiment of a punctal plug.

Referring now to the discussion that follows and also to the drawings, illustrative approaches to the disclosed devices and methods are shown in detail. Although the drawings represent some possible approaches, the drawings are not necessarily to scale and certain features may be exaggerated, removed, or partially sectioned to better illustrate and explain the present disclosure. Further the descriptions set forth herein are not intended to be exhaustive or otherwise limit or restrict the claims to the precise forms and configurations shown in the drawings and disclosed in the following detailed description.

Referring to FIGS. 1-5, an exemplary arrangement of a punctal plug 10 is illustrated. Punctal plug 10 includes a body portion 12 and a retaining flange 14. Body portion 12 includes an open distal end 16 and an open proximal end 18 that is in communication with retaining flange 14. Formed within body portion 12 is at least one window 20. In one exemplary arrangement, a plurality of windows 20 are formed, separated by land members 22. Windows 20 may be formed so as to be spaced equi-distant from one another. Body portion 12 of punctal plug 10 may be made from a biocompatible material such as titanium, stainless steel, plastics, elastomers or any other material which may be formed into body portion 12.

In one exemplary arrangement, at least one cross-member 24 is disposed within body portion 12. Alternatively, a pair of cross-members 24 is provided. Each cross-member 24 is defined by ends 25 that are fixedly secured to an inner wall 26 of body portion 12. In one exemplary arrangement, cross-members 24 are arranged within body portion 12 in an intersecting manner, such that one cross-member 24a is disposed above the other cross-member 24b. In another exemplary arrangement, cross-members 24a, 24b are integrally connected together so as to lie along a common plane (not shown). Cross-members 24 are also constructed of a biocompatible material, whereby the material allows for some degree of flexibility, as will be explained below in further detail.

Retaining flange 14 is defined by a distal end 28 and a proximal end 30. Distal end 28 is defined by a diameter that generally corresponds to the diameter of proximal end 18 of body portion 12. Proximal end 30 is defined by a diameter that is larger than the diameter of distal end 28 and body portion 12. In one exemplary arrangement, an interior surface 32 slopes outwardly from distal end 28 to proximal end 30.

As shown in FIG. 1, a delivery device 34 is shown releasably connected to punctal plug 10. More specifically, delivery device 34 includes a delivery cannula 36 having a distal end that secures to interior surface 32 of retaining flange 14. In one exemplary arrangement, the distal end of delivery cannula 36 includes retaining apertures (not shown) that releasably receives retaining members 38 that extend from interior surface 32. More specifically, retaining members 38 may be constructed of a flexible material that permits selective engagement and disengagement between punctal plug 10 and delivery cannula 36. Alternatively, the distal end of delivery cannula 36 may be provided with retaining members that engage complementary retaining apertures (not shown) formed on interior surface 32. Other suitable mechanisms for releasably securing punctal plug 10 to deliver cannula 36 are also within the scope the present disclosure.

Figure 4:
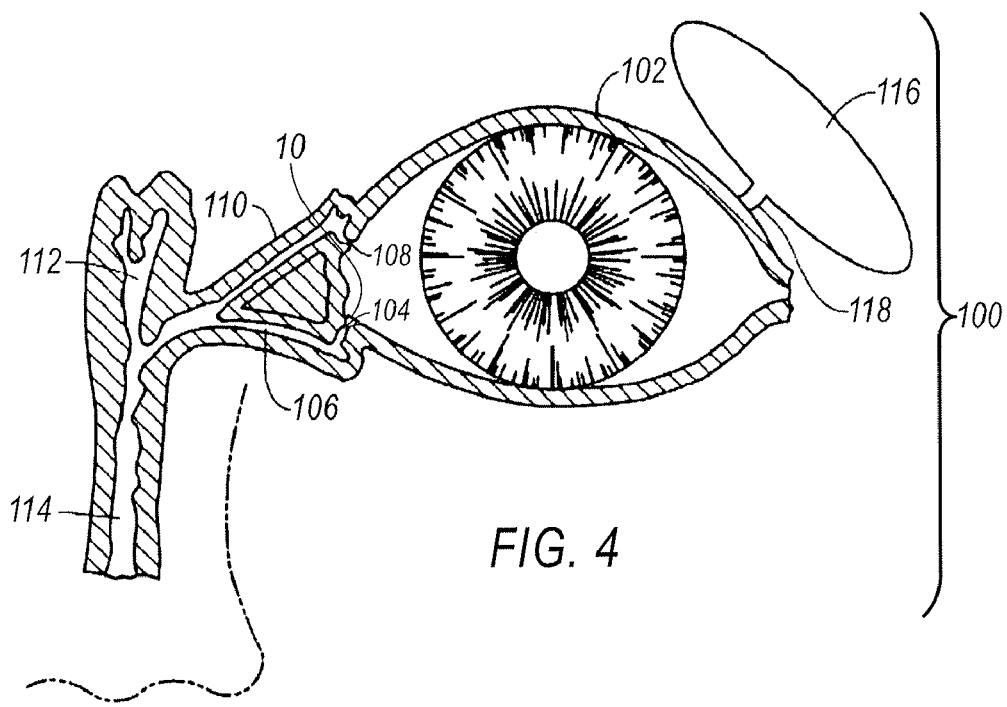
FIG. 4 is a front, partially sectional view of a lacrimal duct system of a mammalian eye with a punctal plug disposed therein.
Figure 5:
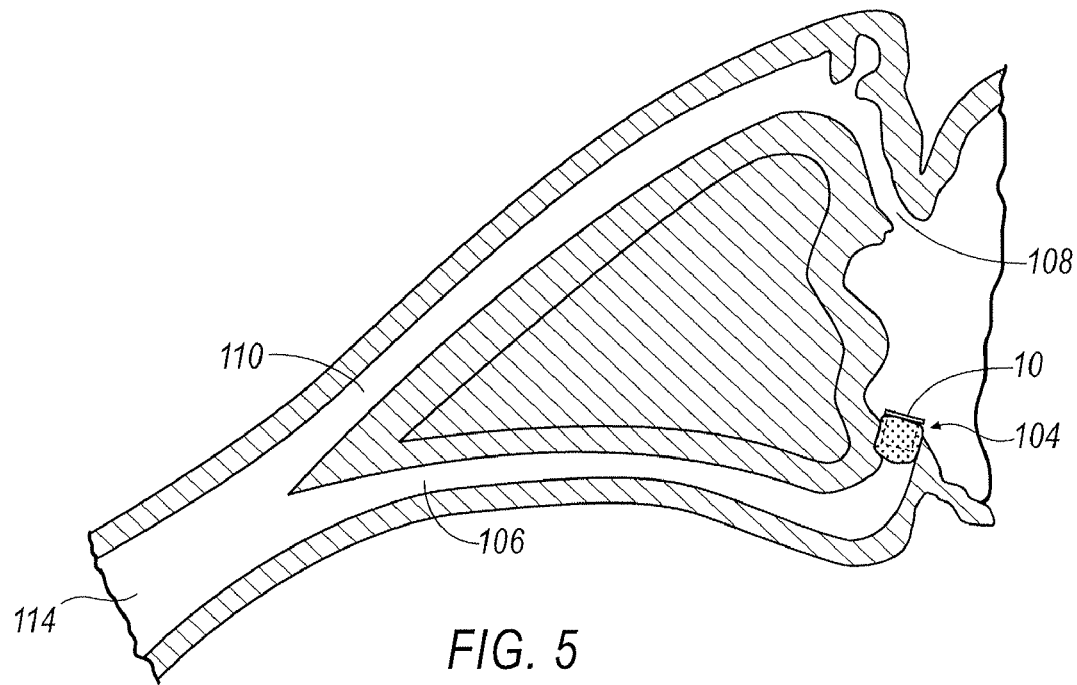
FIG. 5 is an enlarged front sectional view of the lacrimal canaliculi of FIG. 4, with a punctal plug disposed therein.

Turning now to FIGS. 4 and 5, the lacrimal duct system 100 of a mammalian eye 102 will be described. System 100 includes a lower punctum 104 connected to a lower lacrimal canaliculus 106, and an upper punctum 108 connected to an upper lacrimal canaliculus 110. Canaliculli 106 and 110 are connected to a lacrimal sac 112 and a nasolacrimal duct 114. A lacrimal gland 116 is connected to eye 102 via a lacrimal duct 118. In general, tears are produced by lacrimal gland 116 and are provided to eye 102 via lacrimal duct 118, and tears are drained from 102 via punctum 108 and canaliculus 110, punctum 104 and canaliculus 106, and nasolacrimal duct 114.

Figure 3:
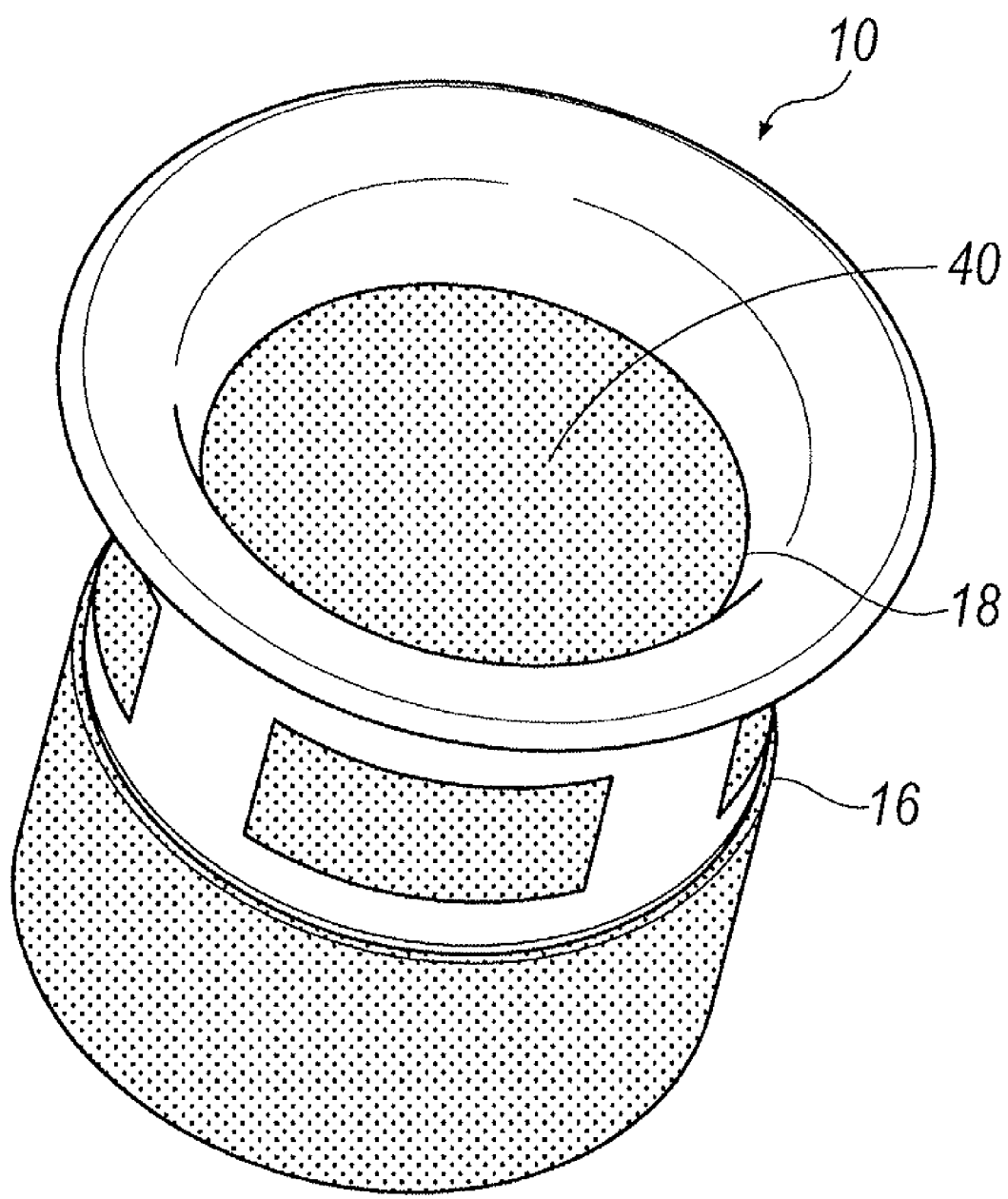
FIG. 3 is a perspective view of the punctal plug of FIG. 2 with an exemplary therapeutic compound disposed therein.

In operation, punctal plug 10 is secured to the distal end of delivery cannula 36. Delivery cannula 36 is secured to a suitable drug supply. Once secured to delivery cannula 36, but before a drug 40 is injected into punctal plug 10 via delivery cannula 36, distal end 16 is implanted into either lower or upper punctums 104, 106. In FIGS. 4 and 5, distal end 16 of body portion 12 of punctal plug 10 is implanted into lower punctum 104 until retaining flange 14 contacts an outer surface of the eye. Once positioned, a suitable therapeutic drug is injected through delivery cannula 36 and into punctal plug 10. More specifically, a phase transition drug formulation 40 is injected through delivery cannula 36 into punctal plug 10. Because body portion 12 includes at least one window 20, a portion of phase transition drug formulation 40 flows through window 20 and some also flows out distal end 16 of body portion 12, as shown in FIG. 3. This action causes drug formulation to conform to the irregular shape of the walls of lower punctum 104. As drug formulation 40 cools, it solidifies into a drug bolus such that the drug formulation 40 serves to lock punctal plug 10 into place in lower punctum 104, thereby preventing migration of punctal plug 10, as well as preventing inadvertent dislodgement of punctal plug 10 from punctum 104. As shown in FIG. 5, because drug formulation is able to conform to the irregularities in shape of the punctum, puntal plug 10 is able to adapt to various contours of the respective punctums without requiring unique geometry for each plug 10 for each individual into which the puntal plug 10 is inserted.

Further, when injected, drug formulation 40 also flows around cross-members 24. Because cross-members 24 have some degree of flexibility, as drug formulation 40 flows into punctal plug 10, cross-members 24 serve to generally retain the basic shape of punctal plug 10 to keep punctal plug 10 properly positioned within the punctum 104, but allow some degree of flexing of body portion 12. Further, as drug formulation 40 cools, the drug bolus attaches to cross-members 24, thereby locking the drug bolus into punctal plug 10, such that the drug bolus itself is prevented from migrating down punctums 104 and 106. Windows 20 also may aid in the locking effort.

Once drug formulation 40 has been injected and permitted to solidify, punctal plug 10 is released from delivery cannula 36, thereby leaving punctal plug 10 in place within the eye. In one embodiment, forceps may be utilized to release delivery cannula 36 from punctal plug 10. Drug formulation 40, which is retained within punctal plug 10, is configured to allow for sustained release of ophthalmic drugs over a predetermined period of time (e.g., 3-6 months). Other predetermined time periods are also possible (e.g., 1-2 days, 1-2 months, 1 year, etc). As drug formulation 40 is released into the patient over time, the drug bolus shrinks such that punctal plug detaches from the interior wall of punctum 104, 106. Once so released, punctal plug 10 may be easily removed in a non-invasive manner.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A punctal plug, comprising:
a body portion; and
a retaining flange;
wherein the body portion is defined by an open distal end, an open proximal end and a wall portion, wherein the wall portion further includes at least one window extending therethrough such that at least some of a drug formulation injected into the body portion will flow through at least one of the at least one windows and wherein at least some of the drug formulation injected into the body portion will flow out the open distal end; and wherein the retaining flange is configured to have an outer periphery that is larger than the outer periphery of the body portion.

2. The punctal plug of claim 1, wherein the body portion further comprises a plurality of windows formed therein, wherein the windows are located equi-distant from one another.

3. The punctal plug of claim 1, wherein the retaining flange is defined by a distal end and a proximal end, wherein the distal end is fixedly connected to the proximal end of the body portion and has an outer periphery that is substantially the same size and configuration as an outer periphery of the proximal end of the body portion.

4. The punctal plug of claim 3, wherein the retaining flange is contoured outwardly toward the proximal end of the retaining flange.

5. The punctal plug of claim 1, wherein the retaining flange further comprises at least one retaining member formed thereon, wherein the retaining member is configured for releasably attaching to a delivery cannula.

6. The punctal plug of claim 5, wherein the retaining member is an inwardly extending protrusion.

7. The punctal plug of claim 1, wherein the body portion and retaining flange are constructed of a biocompatible material.

8. A punctal plug, comprising:
a body portion; and
a retaining flange;
at least one cross-member, wherein the cross-member is defined by first and second ends that are fixedly secured to an interior surface of the wall portion of the body portion;
wherein the body portion is defined by an open distal end, an open proximal end and a wall portion, wherein the wall portion further includes at least one window extending therethrough; and
wherein the retaining flange is configured to have an outer periphery that is larger than the outer periphery of the body portion.

9. The punctal plug of claim 8, comprising a pair of cross-members, wherein a first cross-member is positioned above a second cross member.

10. The punctal plug of claim 9, wherein the cross-members are arranged such that the cross-members intersect one another.

11. The punctal plug of claim 8, comprising a pair of cross-members integrally connected together so as to intersect one another and such that the cross-members lie in the same plane.

* * * * *